United States Patent [19]

Ochsner

[11] Patent Number: 4,654,169

[45] Date of Patent: Mar. 31, 1987

[54] PHENYL-ALIPHATIC OXIMES AS ODORANTS

[75] Inventor: Paul A. Ochsner, Geneva, Switzerland

[73] Assignee: Givaudan Corporation, Clifton, N.J.

[21] Appl. No.: 822,978

[22] Filed: Jan. 27, 1986

[30] Foreign Application Priority Data

Feb. 6, 1985 [CH] Switzerland ........................ 527/85

[51] Int. Cl.$^4$ ........................ C11B 9/00; C07C 131/00

[52] U.S. Cl. ........................ 252/522 R; 564/253; 564/259; 564/267; 564/268

[58] Field of Search ........................ 252/522 R; 564/259, 564/265, 267, 253

[56] References Cited

U.S. PATENT DOCUMENTS 4,052,194 10/1977 Wilcox ........................ 564/268
4,284,814 8/1981 DeSimone ........................ 564/253
4,426,321 1/1984 Ochsner ........................ 564/268
4,544,714 10/1985 Ochsner ........................ 252/522

FOREIGN PATENT DOCUMENTS 101178 4/1986 European Pat. Off. ........ 252/522 R

OTHER PUBLICATIONS

Swiss Patent Application No. 645/82, filed Feb. 3, 1982 (not published) with copy of verified English language translation of same.

*Primary Examiner*—Werren B. Lone
*Attorney, Agent, or Firm*—Robert F. Tavares

[57] ABSTRACT

The invention concerns the novel odorants 2,2,4-trimethyl-1-phenyl-3-pentanone oxime, 2,4,4-trimethyl-5-phenyl-3-hexanone oxime and 2,4,4-trimethyl-5-phenyl-3-heptanone oxime, a process for making same, odorant compositions containing same and methods for preparing improved odorant compositions using same.

16 Claims, No Drawings

PHENYL-ALIPHATIC OXIMES AS ODORANTS

THE INVENTION

The invention concerns novel oximes of the formula

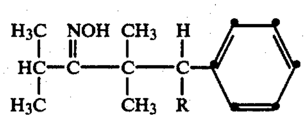

I wherein R is hydrogen, methyl or ethyl, processes for the manufacture of these compounds, and their use as odorants.

Formula I is intended to embrace both the syn- and anti-forms of the oximes, with the anti-form being preferred.

DESCRIPTION OF THE PREFERRED EMBODIMENTS

The novel oximes of formula I can be prepared by a process which comprises reacting a ketone of the formula

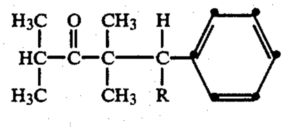

II wherein R is as defined above, with hydroxylamine or a salt thereof

The reaction of a ketone of formula II with hydroxylamine or a salt thereof can be carried out according to methods known per se. (See e.g. Organikum, Organisch-chemisches Grundpraktikum, collective authors; 7th Edition; VEB Deutscher Verlag der Wissenschaften; Berlin 1967, 375, 555.) When the hydroxylamine salt is used the oxime is readily obtained by reacting the ketone with the salt (for example, the hydrochloride or sulphate) in alcoholic solution or aqueous-alcoholic solution containing pyridine or sodium acetate. The reaction temperature is preferably the reflux temperature of the reaction mixture. The resulting oxime can be separated from the reaction mixture by known methods.

The working-up is conveniently carried out according to methods known per se: distilling off the majority of the alcohol, adding an organic solvent, washing with water and finally removing the unreacted ketone.

The ketone starting materials of formula II are known or can be prepared according to known methods, for example, by chain-lengthening commercially available diisopropyl ketone (e.g. by means of arylalkyl halides).

The compounds of formula I have particular organoleptic properties which make them especially suitable as odorant substances.

The oximes provided by the present invention are distinguished by a particular combination of perfumistically valuable properties. They are all either colorless (or at most slightly colored), readily accessible, the individual batches are constant in odor, non-irritating, stable, and easy to handle.

The compound of formula I are generally reminiscent with respect to odor of notes of blackcurrants, sage, and grapes. The individual olfactory notes are the following:

Compound I:

$R{=}H$:

powerful and long-lasting odor, green, natural, after sage, after blackcurrants, but more flowery;

Compound I:

$R{=}CH_3$:

powerful and very natural odor after sage, grapes, wine pressing shed;

Compound I:

$R{=}C_2H_5$:

powerful and diffusive odor, after blackcurrants.

These olfactory notes are quite different from those disclosed for the araliphatic oxime 3-benzylpentan-2-one oxime in Swiss Patent Application No. 645/82 (which became accessible on Aug. 10, 1983 with the publication of European Patent Publication No. 85,352) and which compound is described as smelling like ginger nuts, pyrazine and peas. Additionally, the novel oximes of the present invention are found to be about one hundred times greater in olfactory strength than the known oxime (compounds tested as 1% solutions in isopropyl myristate applied to smelling strips, measured immediately and/or after 24 hours). Thus the novel oximes may be used in more diluted form.

On the basis of their natural odor notes and their fixation (long-lasting effect, especially with respect to freshness) they are suitable, in particular, for modifying known compositions, examples of such compositions being:

(a) flowery compositions in which, for example, the citrus notes are to be intensified (e.g., for cologne types and the like, as well as extracts), (b) fruity compositions, for example of the currant type (extract types), compositions of the feminine as well as of the masculine direction, (c) compositions with green notes, where especially a desired natural effect is produced, and finally (d) compositions in which generally the character of natural oils is striven for (e.g. lilac or lavender).

The compounds of formula I combine with numerous known natural or synthetic ingredients of odorant substance compositions, whereby the range of the natural ingredients can embrace not only readily-volatile but also semi-volatile and slightly-volatile components and the range of the synthetic ingredients can embrace representatives from almost all classes of substances, as will be evident from the following compilation:

Natural products, such as angelica seed oil, tree moss absolute, basil oil, mugwort oil, bergamot oil, castoreum, acetylated cedarwood oil (e.g. Vertofix ® IFF or Cedartone TM Givaudan), coriander oil, oak moss, elemi oil, galbanum oil, geranium oil, jasmine absolute and its substitute, camomile oil, lavandin oil, lavender oil, mandarin oil, mastix absolute, clove bud oil, neroli oil, patchouli oil, petitgrain oil Paraguay, rose oil, rosemary oil, sandalwood oil, styrax, vetiver oil, wormwood oil, ylang-ylang oil, hyssop oil, civet oil, lemon oil.

Alcohols, such as citronellol, dimethylbenzylcarbinol, Dimetol ® Giv. (2,6-dimethyl-2-heptanol), geraniol, linalool, menthol, 3-methyl-5-(2′,2′,3′-trimethylcyclopent-3′-en-1′-yl)-pentan-2-ol (Sandalore ® Givaudan), nerol, phenylethyl alcohol, phenylpropyl alcohol, natural rhodinol, terpineol, a-terpineol, 2,2,8-trimethyl-7-nonen-3-ol, cinnamic alcohol.

Aldehydes, such as α-amylcinnamaldehyde, citral, cyclamen aldehyde, decanal, 3,5-dimethyl-cyclohex-3-ene-carboxaldehyde, n-dodecanal, heliotropin, α-hexylcinnamaldehyde, hydroxycitronellal, methylnonyl acetaldehyde, p-tert.butyl-α-methyl-dihydro-cinnamaldehyde (e.g. Lilial® Givaudan), n-undecen-10-al.

Ketones, such as acetylcedrene, allylionone, p-hydroxybenzyl-acetone, α-ionone, 2,4,4,7-tetramethyl-6,8-nonadien-3-one, p-methylacetophenone, methylionone, 1,2,3,4-tetrahydro-1,1-dimethyl-4-propionylnaphthalene.

Esters, such as ethyl acetoacetate, 3-ethyl-1,1-dimethyl-cyclohex-3-ene-2-carboxylic acid ethyl ester (Givescone TM Givaudan), 3-ethyl-1,1,4-trimethyl-cyclohex-3-ene-2-carboxylic acid ethyl ester (Myrascone TM Givaudan), allyl phenoxyacetate, amyl salicylate, benzyl acetate, benzyl salicylate, bornyl acetate, cedryl acetate, cinnamyl formate, cis-3-hexenyl acetate, cis-3-hexenyl benzoate, geranyl acetate, hexyl salicylate, isobutyl salicylate, linalyl acetate, linalyl anthranilate, methyl dihydrojasmonate, 4-[4-methyl-3-pentenyl]-cyclohex-3-en-1-yl-carbinyl acetate (e.g. Myraldylacetat TM Givaudan), oxyoctalin formate Giv. ($\Delta^1$-1,5,9,10-tetramethyl-5-formoxy-octalin), phenylethyl acetate, styrallyl acetate, terpenyl acetate, p-tert.butyl-cyclohexyl acetate.

Lactones, such as coumarin, γ-decalactone, γ-dodecalactone, γ-nonalactone, γ-undecalactone.

Various additional components often used in perfumery, such as acetaldehyde-propylphenyl-ethyl acetal, cyclocitrylideneacetonitrile, 1,1-dimethyl-4-acetyl-6-tert.butylindane, dodecahydro-3a,6-6-9a-tetramethyl(2,1-b)furan, eugenol, Galaxolid® IFF (7-acetal-1,1,3,4,4,6-hexamethyltetralin), indole, isobutylquinoline, p-menthane-8-thiol-3-one, methyleugenol, methyl 1 methyl-cyclododecyl ether (e.g. Madrox TM Givaudan), musk compounds (musk ketone, 12-oxahexadecanolide (e.g. Musk 174 TM Naarden), 8,12-oxido-13,14,15,16-tetranorlabdane (Fixateur 404 TM).

The compounds of formula I can be used in wide limits which can extend in compositions, for example, from 0.01 (detergents)-50% (alcoholic solutions). It will be appreciated, however, that these values are not limiting values, as the experienced perfumer can also achieve effects with even lower concentrations or can synthesize novel complexes with even higher amounts. The preferred concentrations range between 0.05 and 10%. The compositions manufactured with I can be used for all kinds of perfumed consumer goods (eau de cologne, eau de toilette, extracts, lotions, creams, shampoos, soaps, salves, powders, deodorants, detergents, tobacco, etc.).

The compounds I can accordingly be used in the manufacture of compositions and, as will be evident from the above compilation, a wide range of known odorant substances can be used. In the manufacture of such compositions the known odorant substances enumerated above can be used according to methods known to the perfumer, such as e.g. from W. A. Poucher, Perfumes, Cosmetics and Soaps 2, 7th Edition, Chapman and Hall, London, 1974.

EXAMPLE 1

(a) 100 g of hydroxylamine hydrochloride are dissolved in 1 liter of ethanol and 100 g of pyridine in a round flask which is provided with a stirrer, a thermometer and a condenser. The mixture is stirred at room temperature for a quarter of an hour and 100 g of the ketone II, R=H, namely 2,2,4-trimethyl-1-phenyl-3-pentanone, are added to the solution. The reaction mixture is held at reflux temperature for 2 hours. Thereupon, the majority of the ethanol, namely about $\frac{3}{4}$, is distilled off. After cooling the residue is poured on to ice-water and taken up in ether. The ethereal solution is washed as follows: firstly with water, thereupon with 5% dilute hydrochloric acid in order to eliminate the excess pyridine and then again with water until neutral. After evaporation of the ether there are obtained 99 g of the crude oxime I (with R=H) which still contain 77 g of unreacted ketone. This ketone (b.p. 90° C./1.5 mmHg) is distilled off.

The residue now consists of the crude oxime.

IR spectrum: typical bands at 3250 $cm^{-1}$ (broad), 1660 $cm^{-1}$ (moderately strong), 930 $cm^{-1}$ (strong).

NMR: (60 MHz, $CDCl_3$) $\delta=9.7$ (broad).

This crude oxime can be used in perfumery e.g. in the form of a 10%, or even a 1%, solution in isopropyl myristate.

(b) When 2,4,4-trimethyl-5-phenyl-3-hexanone is used as the starting material in the above process there is obtained 2,4,4-trimethyl-5-phenyl-3-hexanone oxime;

IR spectrum; typical bands at 3250 $cm^{-1}$ (broad), 1650 $cm^{-1}$ (weak), 935 $cm^{-1}$ (strong).

NMR: (60 MHz, $CDCl_3$) $\delta=9.2$ (broad).

(c) When 2,4,4-trimethyl-5-phenyl-3-heptanone is used as the starting material in the above process there is obtained 2,4,4-trimethyl-5-phenyl-3-heptanone oxide;

IR spectrum: typical bands at 3300 $cm^{-1}$ (broad), 1650 $cm^{-1}$ (weak), 940 $cm^{-1}$ (strong).

The 2,4,4-trimethyl-5-phenyl-3-heptanone is obtainable by alkylating diisopropyl ketone with 1-chloro-1-phenyl-propane; b.p.: 78°-79° C./0.2 mmHg.

IR spectrum: typical bands at 1705 $cm^{-1}$ (strong).

EXAMPLE 2

A. Cologne composition

| | Parts by weight |
|---|---|
| Bergamot oil | 80 |
| 2-Ethyl-3,6,6-trimethyl-2-cyclohexen-1-yl-carboxylic acid ethyl ester | 80 |
| Galaxolide ® 50 (in ethyl phthalate) (1,3,4,6,7,8-hexahydro-4,6,6,7,8,8-hexamethylcyclopenta-γ-2-benzo-pyran)IFF | 120 |
| Hydroxycitronellal | 60 |
| Methyl 1-methylcyclododecyl ether | 60 |
| Bornyl acetate | 40 |
| Musk ketone | 40 |
| Givescone TM Giv (2-ethyl-6,6-dimethyl-2-cyclohexane-1-carboxylic acid ethyl ester) | 20 |
| Petitgrain oil | 20 |
| Sandalore ® Giv (3-methyl-5-(2,2,3-trimethylcyclopent-3-en-1-yl)pentan-2-ol) | 30 |
| Tree moss absolute | 5 |
| | 395 |

By adding 50 parts by weight of a 10% solution of the—preferred—compound I (with R=H) the resulting cologne base becomes much more natural. The somewhat camphorous note of the bornyl acetate, which was observed previously, is enveloped by the addition of the oxime. At the same time, the sandal note of Sandalore® is further brought into prominence. The effect achieved with the addition of the oxime corresponds to the effect which would be achieved by adding a natural product.

B. When 50 parts by weight of a 1% solution of the compound I ($R{=}CH_3$) in isopropyl myristate is added to the cologne composition of Example 2, the resulting base becomes fresher and greener. The camphorous note is enveloped and the petitgrain oil comes into prominence, thereby the natural character of the resulting composition gains extraordinarily.

C. Spicy base

| | Parts by weight |
|---|---|
| Benzyl acetate | 100 |
| Hydroxycitronellal | 100 |
| Phenylethyl alcohol | 100 |
| Amyl salicylate | 100 |
| Patchouli oil | 80 |
| Ylang-ylang oil | 50 |
| Eugenol | 50 |
| Linalyl acetate | 60 |
| Musk ketone | 50 |
| Cedryl acetate | 30 |
| Epoxycedrene | 30 |
| Acetylcedrene | 30 |
| Coumarin | 30 |
| Spearmint oil | 15 |
| Thyme oil | 15 |
| Lemon oil | 5 |
| Dipropylene glycol | 105 |
| | 950 |

The addition of 50 parts by weight of a 10% solution of 2,2,4-trimethyl-1-phenyl-3-pentanone oxime in isopropyl myristate confers more freshness and more life to the above base. The phenolic, somewhat medicinal, secondary odour disappears in favour of a minty, fresh, light note. The spicy note is sharper, dryer, more herby, with a nuance after blackcurrants. The base is especially suitable for masculine perfume.

I claim:

1. A compound of the formula

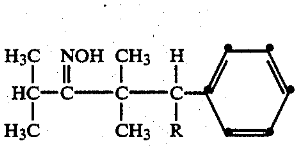
I wherein R is hydrogen, methyl or ethyl.

2. The compound in accordance with claim 1 which is 2,2,4-trimethyl-1-phenyl-3-pentanone oxime.

3. The compound in accordance with claim 1 which is 2,4,4-trimethyl-5-phenyl-3-hexanone oxime.

4. The compound in accordance with claim 1 which is 2,4,4-trimethyl-5-phenyl-3-heptanone oxime.

5. An odorant composition which comprises an olfactorily effective amount of a compound of the formula

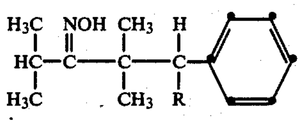
I wherein R is hydrogen, methyl or ethyl, and at least one other olfactory agent.

6. The composition in accordance with claim 5 wherein the compound is 2,2,4-trimethyl-1-phenyl-3-pentanone oxime.

7. The composition in accordance with claim 5 wherein the compound is 2,4,4-trimethyl-5-phenyl-3-hexanone oxime.

8. The composition in accordance with claim 5 wherein the compound is 2,4,4-trimethyl-5-phenyl-3-heptanone oxime.

9. A method for improving the odor of an odorant composition which comprises adding thereto an olfactorily effective amount of a compound of the formula

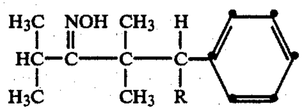
I wherein R is hydrogen, methyl or ethyl.

10. The method in accordance with claim 9 wherein the compound to be added is 2,2,4-trimethyl-1-phenyl-3-pentanone oxime.

11. The method in accordance with claim 9 wherein the compound to be added is 2,4,4-trimethyl-5-phenyl-3-hexanone oxime.

12. The method in accordance with claim 9 wherein the compound to be added is 2,4,4-trimethyl-5-phenyl-3-heptanone oxime.

13. A process for the manufacture of a compound of the formula

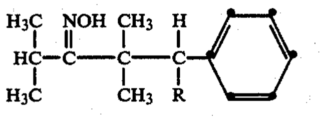
I wherein

R is hydrogen, methyl or ethyl, which comprises reacting a compound of the formula

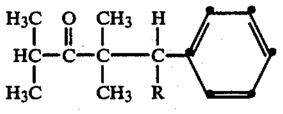
II wherein

R is as defined above, with hydroxylamine or a salt thereof.

14. The process in accordance with claim 13 wherein the compound manufactured is 2,2,4-trimethyl-1-phenyl-3-pentanone oxime.

15. The process in accordance with claim 13 wherein the compound manufactured is 2,4,4-trimethyl-5-phenyl-3-hexanone oxime.

16. The process in accordance with claim 13 wherein the compound manufactured is 2,4,4-trimethyl-5-phenyl-3-heptanone oxime.

* * * * *